United States Patent [19]
MacConnell

[11] Patent Number: 5,217,593
[45] Date of Patent: Jun. 8, 1993

[54] NUCLEIC ACID PURIFICATION SYSTEM AND METHOD

[76] Inventor: William P. MacConnell, 1849 Rubenstein Dr., Cardiff, Calif. 92007

[21] Appl. No.: 911,515

[22] Filed: Jul. 10, 1992

Related U.S. Application Data

[63] Continuation-in-part of Ser. No. 668,856, Mar. 13, 1991, Pat. No. 5,139,637.

[51] Int. Cl.[5] .................. G01N 27/26; G01N 27/447
[52] U.S. Cl. .......................... 204/299 R; 204/182.1; 204/182.8; 204/301
[58] Field of Search .............. 204/182.8, 301, 299 R, 204/182.1, 182.9

[56] References Cited

U.S. PATENT DOCUMENTS

| | | | |
|---|---|---|---|
| 3,255,100 | 7/1966 | Raymond | 204/180 |
| 3,902,986 | 9/1975 | Nees | 204/299 |
| 3,969,218 | 7/1976 | Scott | 204/299 |
| 3,989,612 | 11/1976 | Kragt et al. | 204/180 |
| 4,049,534 | 9/1977 | Posner | 204/299 |
| 4,159,933 | 7/1979 | Allington | 204/299 R X |
| 4,164,464 | 8/1979 | Allington | 204/299 |
| 4,576,702 | 3/1986 | Peck et al. | 204/299 |
| 4,576,703 | 3/1986 | Peck et al. | 204/299 |
| 4,617,102 | 10/1986 | Tomblin et al. | 204/299 R |
| 4,634,513 | 1/1987 | Asao | 204/301 |
| 4,699,706 | 10/1987 | Burd et al. | 204/301 |
| 4,707,233 | 11/1987 | Margolis | 204/182.3 |
| 4,725,348 | 2/1988 | Diekmann | 204/299 |
| 4,747,918 | 5/1988 | Wassenberg, II | 204/182.8 |
| 4,824,547 | 4/1989 | Zhang et al. | 204/299 |
| 4,859,302 | 8/1989 | Alfenito | 204/182.8 |
| 4,863,582 | 9/1989 | Wijangco et al. | 204/299 R |
| 5,102,518 | 4/1992 | Doering et al. | 204/180.1 |

FOREIGN PATENT DOCUMENTS

| | | | |
|---|---|---|---|
| 1583819 | 8/1990 | U.S.S.R. | 204/299 R |
| 2148326 | 5/1985 | United Kingdom | 204/301 |

*Primary Examiner*—John Niebling
*Assistant Examiner*—John S. Starsiak, Jr.
*Attorney, Agent, or Firm*—Baker, Maxham, Jester & Meador

[57] ABSTRACT

A process for the purification of DNA and the like comprises a housing having walls forming a reservoir having a chamber for containing a buffer solution, means for circulating a buffer through the reservoir, a disposable cassette within said chamber having first means including a gel for defining a first path extending between an inlet end and an outlet end, a well for introducing a bacterial sample into the path at said inlet end thereof, and a second path intersecting the first path via an elution chamber, having a collection chamber including an elution window at said outlet end, and an electrical circuit for selectively applying an electrical potential along each of the paths for selectively moving a plasmid first along the first path from the bacterial well to the elution chamber, then along the second path to the collection window at the end thereof.

22 Claims, 2 Drawing Sheets

NUCLEIC ACID PURIFICATION SYSTEM AND METHOD

REFERENCE TO RELATED APPLICATION

The present application is a continuation-in-part of co-pending application Ser. No. 07/668,856, now U.S. Pat. No. 5,139,637 filed Mar. 13, 1991 and entitled PLASMID PURIFICATION SYSTEM AND METHOD.

BACKGROUND OF THE INVENTION

The present invention relates to the purification of nucleic acids and pertains particularly to an improved method and apparatus for the purification of nucleic acids, plasmids and the like.

A great deal of laboratory research is carried out in which recombinant DNA techniques are utilized. Among the research activities carried out are DNA sequencing, DNA restriction mapping, DNA probe generation, construction of other plasmid or related DNA from smaller pieces, RNA transcription from a plasmid template, hybridization blot analysis, transformation into bacterial, yeast or mammalian cells, S1 nuclease mapping, microinjection into embryos, and election microscopy analysis. All of these require substantially pure concentrations of plasmid DNA.

Many techniques and apparatus exist for small scale purification of plasmid DNA. The typical prior art approach to the purification of plasmids involves a series of steps, including a collection of cells grown in liquid culture by centrifugation, separation of the bacterial chromatic (genomic) DNA, and cellular debris from the soluble contents of the bacteria by centrifugation of filtration, and concentration of the plasmid DNA apart from other cellular components by alcohol or isopropanol, absorption to solid media (i.e. ion exchange resin, glass powder, reverse phase chromatography resin, etc.), or salt precipitation. Additional purification steps may be added to these, such as phenol/chloroform extraction, secondary alcohol precipitation, protease or ribonuclease treatment to further purify the plasmid DNA.

Other methods of plasmid purification include the additional steps of the addition of CsCl to supernatnat from the bacterial lysis after removal of the bacterial genomic DNA, followed by ultracentrifugation. The ultracentrifugation results in a CsCl density gradient in which the plasmid DNA forms a sharp band. This band is removed from the gradient, and the DNA separated from the CsCl by alcohol precipitation or other suitable means. These procedures are widely used in molecular biology research for plasmid purification, and have been refined to produce plasmid DNA, which is suitable for use in virtually any subsequent procedure of molecular biology.

Certain apparatus have been developed for purification of plasmid DNA. One such apparatus is available from a company called Applied Biosystems, and can purify DNA from samples of tissue, blood, bacteria, etc. The apparatus utilizes repeated organic extraction of sample material to release and purify the DNA. Reagents drawn from reservoirs are automatically introduced into sample containing vials in which the aqueous/organic extraction occurs. Either phenol or guanidine isothiocynate can be used by the machine as the organic phase material After the extraction steps, the DNA is concentrated on chromatography resin, which is held in the upper portion of the extraction vials. The operator then removes the vials from the instrument and elutes the DNA manually from the resin. This apparatus is designed primarily for purification of genomic DNA from mammalian cells, tissue, blood, etc. and does not perform well with bacterial plasmid DNA. The machine has no capability of separating the plasmid from bacterial DNA.

A fully automated machine is available from Autogen, Inc., which is designed to purify plasmid DNA from recombinant bacteria. This machine is essentially an electronically controlled mechanical robot which performs multiple small scale plasmid purifications. The machine utilizes a precision centrifuge, with sets of disposable plastic tubes into which starting bacterial cultures are placed. Robotic pipet holders positioned above the centrifuge introduce and remove fluids from disposable sample tubes during the run, which involves centrifugation of the samples at two different steps or cycles This machine can purify up to twelve samples of plasmid DNA in less than an hour. However, the machine is extremely expensive for laboratory use.

Other techniques for separation of substance include electrophoresis separation. Exemplary of this approach are the following U.S. Patents:

Strauch, U.S. Pat. No. 3,533,933, granted Oct. 13, 1970, entitled, "Process and Device for the Isolation of Fractions of a Substance Mixture Electrophoretically Separated in a Carrier Gel", discloses a vertical separation column which is filled partially or completely with a carrier gel, with an elution chamber at the bottom of the column.

Levy, U.S. Pat. No. 3,616,454, granted Oct. 26, 1971, entitled "Method of an Apparatus for Electrophoretic Separation in a Gel Column", discloses an apparatus wherein a specimen is placed in the upper end of a polyacrylamide gel column of an electrophoresis whose lower end terminates at a receptacle containing an elution solution.

Nerenberg, U.S. Pat. No. 3,640,813, granted Feb. 8, 1972, entitled "Adapter for a Macromolecule Separation Device", discloses a gel medium disposed in a vertical column, with an adapter for the lower end of the column containing a gel and channels for fluid ingress to the upper gel surface and egress therefrom.

The following patents are of interest in disclosing related methods and apparatus:
U.S. Pat. No. 3,579,433, granted May 18, 1971;
U.S. Pat. No. 3,715,295, granted Feb. 6, 1973;
U.S. Pat. No. 3,755,121, granted Aug. 28, 1973;
U.S. Pat. No. 3,951,776, granted Apr. 20, 1976; and
U.S. Pat. No. 4,164,464, granted Aug. 14, 1979.

Many of these existing methods and apparatus have a number of drawbacks, and are generally unsatisfactory in that they are expensive and require many complicated steps and procedures. Others are unable to produce satisfactory purity and quantities.

In my above identified prior application, I disclose an improved system and method for plasmid purification. However, that system is slower and more complicated than desired.

It is desirable that a simple, rapid, inexpensive, yet reliable method and apparatus for purification of plasmid RNA and DNA starting directly from bacterial culture or collected bacterial cells be available.

SUMMARY AND OBJECTS OF THE INVENTION

It is the primary object of the present invention to provide an improved apparatus and method for the purification of plasmids and the like.

In accordance with a primary aspect of the present invention, an apparatus for the purification of plasmid DNA and the like comprises a housing forming a reservoir or chamber having front and back ends for containing a buffer solution, means for circulating a buffer through said reservoir, disposable means positionable within said housing, and having first means including a gel for defining a first path extending between the front and back ends of said chamber, means for introducing a bacterial sample into said path at a front or inlet end thereof, and second means selectively positionable for defining an elution path extending from the outlet or back end of said first path via an elution chamber at the back end, having a collection window at the back end, and means for selectively applying an electrical potential along each of said paths for selectively moving a plasmid first along said first path from said bacterial sample to the outlet end of said first path, then along said elution path to said collection window at the back end thereof.

BRIEF DESCRIPTION OF THE DRAWING

The above and other objects and advantages of the present invention will become apparent from the following description when read in conjunction with the accompanying drawings wherein.

DETAILED DESCRIPTION OF PREFERRED EMBODIMENTS

Figure 1:
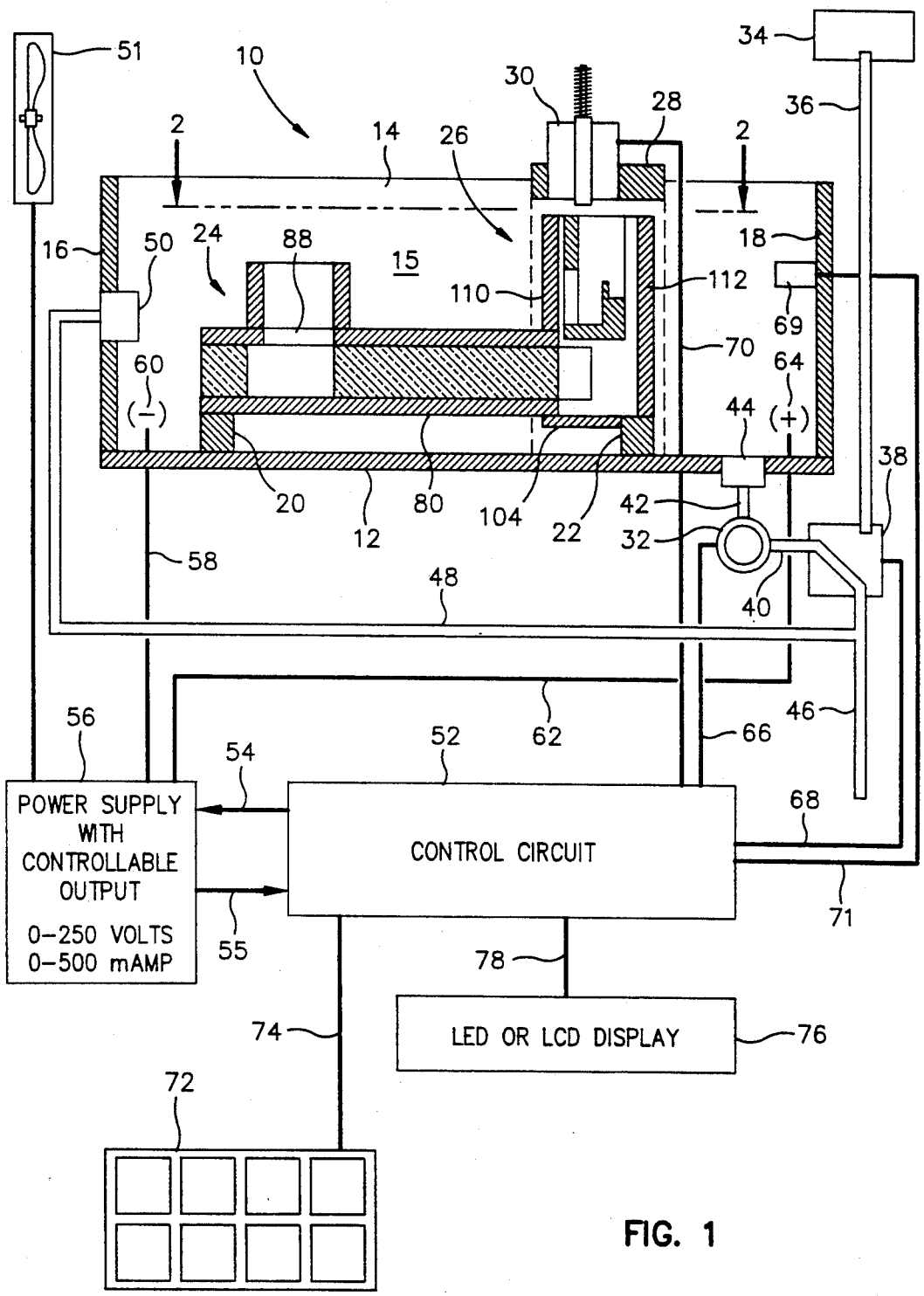
FIG. 1 is a side elevation view illustrating a preferred embodiment of the invention.

Referring to the drawing, and particularly to FIG. 1, there is illustrated a system in accordance with a preferred embodiment of the present invention, designated generally by the numeral 10. The illustrated system comprises a primary or outer housing having a generally box-like open top configuration, with a bottom wall 12, opposed side walls (only one) 14 shown, and opposed end walls 16 and 18 forming a generally open top box-like housing. The housing forms an open top chamber or reservoir for containing a buffer solution which is preferably circulated therethrough. A pair of support members 20 and 22 form a support bracket for the support and mounting of a disposable cassette, designated generally at 24. The disposable cassette 24, to be more fully described, includes a moveable microchamber unit designated generally at 26. A bridge 28 extends between the side walls 14 and mounts a solenoid 30 for moving and activating the microchamber 26 into its operative position.

A buffer circulation and supply system comprises a pump 32 which is connected to a supply reservoir 34 by way of line 36, three way solenoid valve 38 and line 40 to supply buffer fluid via line 42 to a port 44 in the reservoir 15. The pump 32 and valve 38 may be reversed to drain the reservoir via drain line 46. An overflow line 48 connects via an overflow port 50 to the reservoir 15 for maintaining a predetermined or maximum lever of buffer solution in the reservoir. This buffer system may be controlled by a programmable control system that enables the buffer solution to be recirculated and maintained at an optimum level to maintain contact with the gel in the cassette and to be replenished when desired The system is set up to circulate the buffer fluid to maintain and control the pH thereof and to aid in the control of the temperature. A fan 51 may also be used to aid in controlling the temperature of the buffer solution.

A control system comprises a central electronic control circuit 52, which preferably includes a programmable CPU, provides programmed control of the system. The central control unit 54 is connected via a conductor 54 to a power supply 56, which is connected by conductor 58 to a negative electrode 60 at the front or inlet end of the chamber 15. A conductor 62 connects the power supply to a positive electrode 64 at the back or outlet end of the chamber 15. The electrodes are preferably platinum or paddadium wire and apply a variable voltage across the cassette. The central control circuit 52 is also connected by conductor 66 to control the buffer pump 32 and by conductor 68 to control the three way valve 38. A float switch 69 is connected by a conductor 71 to the control circuit. A conductor 70 connects the central control circuit 52 to control the solenoid 30 for activating the microchamber unit 26 by moving it downward into operative position at the outlet end of the cassette 24. A keypad 72 connected by conductor 74 enables programming and control of the central control circuit 52. A LED or LCD display 76 connected by conductor 78 provides visual display of control information.

The cassette is constructed of non-conductive material and generally comprises a pair of vertically spaced apart bottom and top panels 80 and 82 secured between side walls 84 and 86 forming an open ended box-like structure. The panels 80 and 82 are about four inches by three inches and spaced about 0.35 inches apart. This can vary depending on the amount of culture to be processed. A window or opening 88 is formed in the upper panel 82 near the front or inlet end with vertically extending surrounding walls 90, 92, 94, and 96 forming an upstanding well. A plurality of partition walls 98 extend from just ahead of the window at the front end to beyond the ends of the panel at the back end forming a plurality of separate parallel channels 100. The partition walls extend upward through the window 88 forming a separate sample well 102 for each channel. The illustrated cassette has 12 paths or channels, but may have more or less as desired. The housing 10 may be constructed to receive one or a multiple of the multiple channel cassettes.

Figure 3:
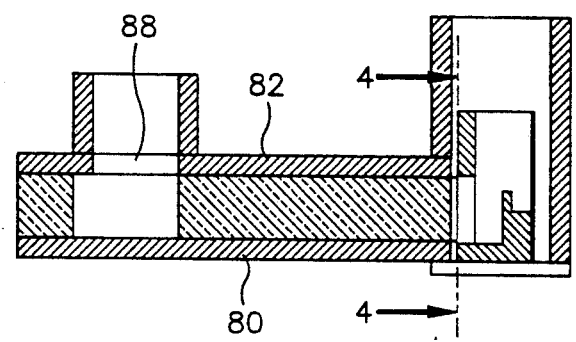
FIG. 3 is a section view taken on line 3—3 of FIG. 2.

The cassette includes an elution well or chamber formed at the back end thereof by a bottom 104, upstanding side walls 106 and 108, and end walls 110 and 112 for receiving the microchamber unit 26 which contains an elution chamber and a collection chamber for each of the channels. The microchamber unit 26 is moveable upward to an inoperative position as shown in FIG. 1 during the separation phase of the procedure, and downward to an active position as shown in FIG. 3 during the elution phase. The inoperative position is above the separation channels of the cassette. The operative position is a lowered position wherein inlets to the elution chambers are aligned with and communicate with outlets of the separation channels of the cassette.

Figure 6:
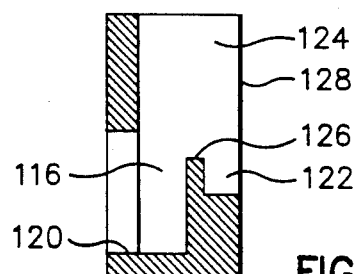
FIG. 6 is a section view taken on line 6—6 of FIG. 5.
Figure 4:
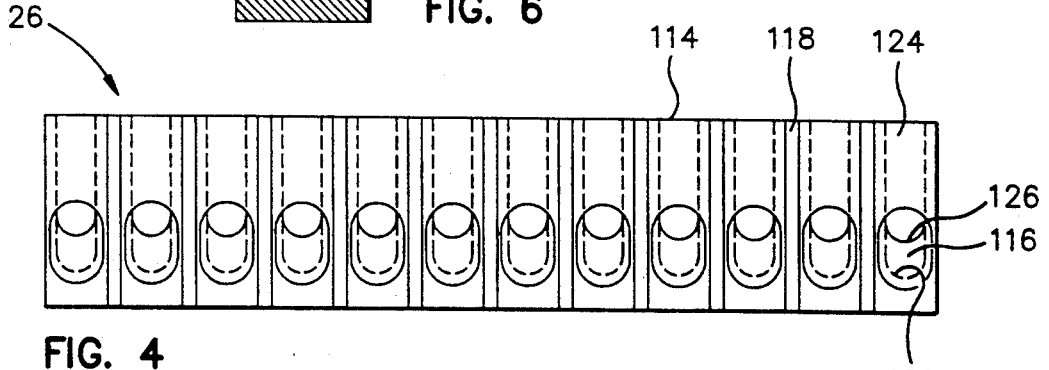
FIG. 4 is a front elevation view taken on line 4—4 of FIG. 3 showing the microchambers.
Figure 5:
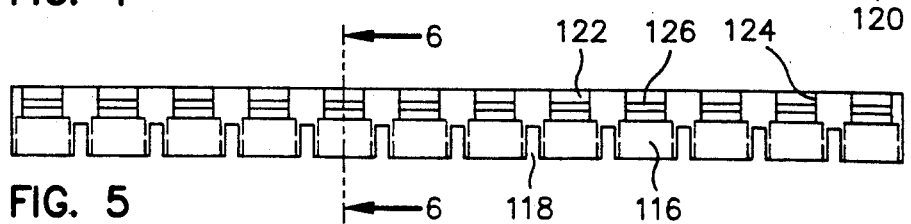
FIG. 5 is a top plan view of the microchambers of FIG. 4.

Referring to FIGS. 4–6, the structure and configuration of an exemplary embodiment of the microchamber unit is illustrated. This unit is constructed of a unitary housing 114 that is formed by milling or molding with an elution chamber 116 for each of the separation channels. The front of the housing is formed of slots 118 between adjacent elution chambers and an inlet port or opening 120 communicating with the outlet of a separation channel 100. The slots 118 are engaged by the outwardly projecting ends of the partition walls 98 and maintain a clear separation between the adjacent channels and adjacent elution chambers.

The elution chamber 116 opens into a sample collection chamber 122 formed by a downwardly extending slot 124, with a separation wall 126 therebetween and having a window or port 128 at the back of the unit. The window or opening is covered by means of a dialysis membrane 128.

The dialysis/ultrafiltration membrane that has proven to give the best results is regenerated cellulose membrane, with an average molecular weight cut off of 50,000 daltons manufactured by Spectrum Medical (Houston, Tex.). Another regenerated cellulose membrane with an average molecular weight cut off of approximately 150,000 daltons is available from Bio Design of New York (Carmel, N.Y.) has also proven to give excellent yields and purity of nucleic acids. Other membranes that have shown good results are the 300,000 and 500,000 dalton molecular weight cut off cellulose ester membranes from Spectrum Medical (Houston, Tex.). The latter two membranes have, however, displayed high background binding phenomena which gives rise to reduced yields of purified nucleic acid. Membranes with molecular weight cut off below 50,000 daltons give poor results due to their ability to trap charged polymers and residual proteins that co-elute from the agarose with the nucleic acid.

The membrane 130 is secured in place over the window by means of a suitable glue or adhesive. The membrane may also be attached or held in place by other means, such as a clamping frame (not shown). Each of the sample chambers 122 are designed to hold 50 microliters after the run has been completed and the surrounding buffer drained. A sample removal hole or opening is provided in the top of the chamber by slot 124 to allow removal of liquid from the chamber. The bottom of the sample chamber 122 has a wall that extends or curves upward of the sides to prevent trapping liquid in the corners of the chamber window. The geometry of the sample chambers and sample removal holes allows a standard 0–200 ul disposable micropipettor tip to be used for removal of fluid from the chamber. The sample chamber geometry also prevents the operator from puncturing the membrane while a disposable tip is fully inserted.

In preparation for a run, the cassette channels are sealed at the front end and sample well and filled with a body of suitable gel, such as agarose gel sandwiched therebetween and exposed at both ends to opposite ends of the chamber 15. A one percent (1%) agarose in an aqueous solution containing 0.02 M Tris-acetate, 0.0005 M EDTA is prepared. The solution is then cooled to fifty degrees Centigrade and poured into the cassette leaving a space at the outlet or elution end. The agarose gel is allowed to solidify and a sample well is cut out directly below the sample loading ports 102. Other suitable gels may be used in place of agarose, such as starch, gelatin or cross-linked versions of agarose, polyacrylamide, starch, or gelatin. Another agarose substitute is available under the trademark Synergel from Diversified Biotech, 46 Marcellus Drive, Newton Centre, Mass. The gel should have a vertical thickness of about three to five tenths (0.30–0.50) inch. The upper panel 82 is formed with a window or opening extending substantially the width thereof. A plurality of spacer walls are disposed between the panels 80 and 82, dividing the space therebetween into a plurality of channels that extend from one end (the inlet wells) to the other for containing an agarose gel, as will be described. Thus, multiple paths (twelve illustrated) extend between the inlet at the front and the outlet at the back end of the cassette.

If the cassettes 24 are to be stored for periods of time greater than one day, 0.01% sodium azide (or other dilute acting anti microbial agent) is added to the agarose buffer prior to pouring into the cassette. In addition, for storage periods of time up to three months, all openings of the cassette are sealed with adhesive tape. Additional protection against dehydration of the agarose is made by sealing the cassette in a suitable plastic bag containing approximately. 0.5 ml of sterile water, with 0.01% sodium azide to maintain humidity in the bag.

When an isolation of nucleic acid is to be carried out, the adhesive tape is removed from the cassette openings. A microchamber block 26, as illustrated in FIGS. 4–6, is prepared with wet dialysis membrane, such as that available from BioDesign of New York, secured to the microchamber block 26 so as to cover all elution windows. The assembled microchamber 26 is loaded into its appropriate spacer in the rear portion of the cassette, as shown in FIG. 1. The microchamber block is kept in position above the agarose (the deactivated position), while the cassette is placed into the electrophoresis rig housing. The electrophoresis chamber is then filled with running buffer, typically 0.02 M Tris-.acetate pH 8.3,0.001 M EDTA, to a level which surrounds the cassette coming into contact and covering the agarose at both ends of the cassette. This level is maintained below the level of the microchamber block, while the latter is in the deactivated mode. The chamber is equipped with an overflow port 50 leading to a drain, which ensures that the above described fluid level is maintained. In the automatic instrument, a float switch is also employed, which indicates to the control circuit to deactivate the filling pump when this level is reached.

For preparation of DNA, bacteria (e.g. *E. coli*) containing plasmid, cosmid, M13 or lambda phage is grown in rich media, such as Circle Grow, 2X YT broth, Terrific Broth (Bio 101, Carlsbad, Calif.), etc. for twelve to sixteen hours at thirty-seven degrees Centigrade. In the case, the *E. coli* containing plasmids or cosmids, such as pUC19, Bluescript or sCOS-1 (Stratagene, San Diego, Calif.) pBR322, etc, we have found that growth of culture in Circle Grow medium in an Erlenmeyer flask at thirty-seven degrees Centigrade for twelve to sixteen hours at 200–250 RPM in a gyratory shaker gives excellent yields.

Sample Lysis and Loading Procedure

Prior to loading, a sample of bacterial culture, such as described above, is first treated with a combination lysis and loading buffer. I have found that adding 0.1 volumes of an aqueous solution containing 60% glycerol, 0.025M Tris.HCl, 0.05 M EDTA, 1% sodium dodecyl sulfate and 200 micrograms/ml of ribonuclease A (Amresco, Solon, Ohio) directly onto the freshly grown culture of bacterial will lyse the bacteria and simultaneously increase the density of lysed solution to greater than the density of the running buffer. Alternatively, the lysis solution can be made up of 10% triton X-100 (Sigma Chemicals), St. Louis, Mo.), 25 mM EDTA, 25 mM Tris-HCl pH 8.0 and 200 mg/ml ribonuclease A. When the latter buffer is used, 0.1 volume is added to the bacterial culture to be lysed. 0.5–10 minutes after lysis and subsequent action of ribonuclease A (RNase) on the bacterial RNA, 50–100 micrograms of proteinase K (Amresco, Solon, Ohio) as a solution in water is added to the lysed bacterial sample. The solution is then mixed by vortexing and incubated at room temperature for five minutes. The RNase treated, and proteinase K treated lysate is then loaded into sample well 102 of the cassette.

Separation and Elution

Running buffer (e.g. 0.02 M Tris.acetate, 0.001 M EDTA) is added to the electrophoresis chamber and approximately 120 volts direct current is applied across the two electrodes 60 and 64, with the positive lead connected to the electrode on the microchamber side of the chamber, and the negative lead connected to the sample port side of the chamber. This voltage is continued for approximately twenty-five minutes until the low molecular weight (i.e. less than 500,000 daltons) charged molecules from each sample electrophoresis through the agarose and out into the running buffer. The voltage during the separation phase can be varied to give optimal separation results for various sizes of DNA. For instance, the separation run might be 25 volts DC for ten minutes followed by 100 volts DC for ten minutes followed by 150 volts DC for ten minutes for a cassette with agarose lane dimensions of 0.28"×0.35"×1.3" with 500 microliters of lysed bacterial loaded. This program would best resolve DNA ranging in size from 3 to 10 kilobases, with the former migrating very close to the end of the agarose lanes. Other voltages and voltage programs might be applied for larger DNA or lower voltage applied for longer time periods to result in better resolution and, therefore, purer DNA.

Figure 2:
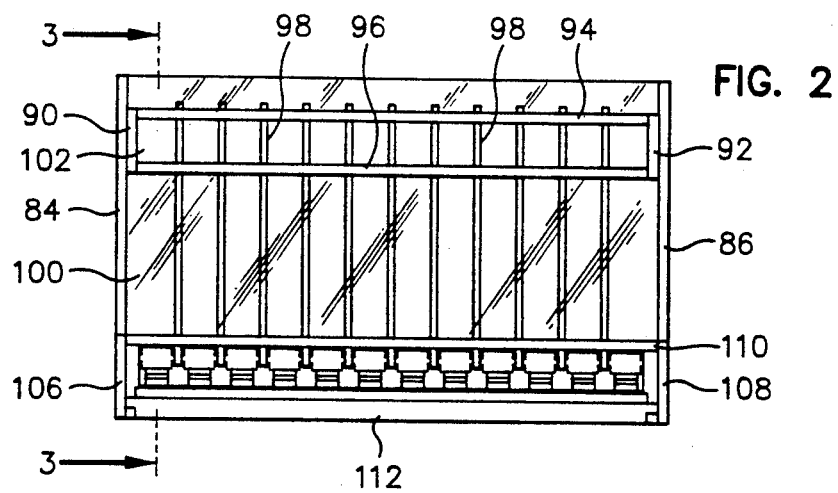
FIG. 2 is a top plan view taken on line 2—2 of the embodiment of FIG. 1.

After the separation stage is complete, and the desired DNA(s) have migrated near the end of the agarose lane, the microchamber 26 with attached membrane 128 is slid downward so as to position its elution chambers directly in front of each respective lane of agarose (FIG. 2). As described above, the microchamber is designed to self-fill with surrounding running buffer. Due to the arrangement of the vanes 98, the ends of which slide into grooves 118 in the microchamber block, a nearly complete seal exists between the lanes of the cassette, so that nucleic acid from one lane cannot migrate into the elution chamber of an adjacent lane. Adding to the above is the fact that electroelution tends to move nucleic acid only in one direction, preventing it from diffusing around the protruding vanes. The lower surface of the microchamber block, however, does not require a seal and, therefore, allows running buffer to seep into the elution and sample chambers when the latter is slid in front of the agarose lanes.

During the elution stage, which is carried out immediately after the above separation stage, 90–150 volts DC is applied across the electrodes in the same direction as before to cause the nucleic acid in the agarose lanes to migrate into the elution chamber 116 of the microchamber block and continue into the sample chambers 122 until it is stopped by the dialysis/ultrafiltration membrane 128. I have found that this process occurs most efficiently at voltages less than 150 volts DC and is adversely affected by higher voltages due to a Donnan effect (Reference: Spectrum Medical Catalogue (1992) pages 131-135) that can occur when too many ions build up at the surface of the dialysis membrane. The ion build up causes the temperature inside the sample chambers to increase and subsequent destruction of the eluted molecules. In practice, 120 volts for 10–45 minutes elutes nearly all of the separated nucleic acid out of the agarose and into the sample chamber. Additional periods of time will cause the bacterial chromatin DNA to elute I have also found that purified nucleic acid is often not only against the membrane but suspended in the sample chamber fluid.

Sample Recovery

When the electrophoresis chamber is drained, the microchamber, except for the sample chamber 122, drains. The purified nucleic acid can then be removed from the sample chambers 122 by pipetting the fluid out through the sample removal holes without having to remove the microchamber block from the gel cassette. The sample chambers are designed to retain 40–50 microliters of fluid once the electrophoresis rig has been drained.

In the automated version of this separation process, the control circuit 52 activates the fluid pump 32 and solenoid valve to fill the electrophoresis chamber from the running buffer reservoir 36. The same control circuit 52 activates a DC power supply 56 to apply voltage to the electrodes 60 and 64 in any one of several programs that can be selected at the beginning of the run by the operator from a touch pad 72 and display 76 on the instrument case. Once the separation stage is completed, the control circuit activates a dampened solenoid 30 that pushes the microchamber block 26 downward in a grove in the gel cassette and against a stop to appropriately position it in front of the agarose lanes. As described above, the microchamber 26 self fills with running buffer shortly after it is pushed into place. The control circuit then applies 90–150 volts DC across the electrodes for 10–45 minutes to complete the elution stage of the run. In the last 30 seconds of this time, the control circuit 52 activates the drain solenoid valve 38, which effects the draining of the running buffer into a discard reservoir connected to the instrument via a flexible tubing. Once the draining is complete, the DC voltages deactivate, and the display on the instrument case indicates to the operator that the run is complete. A typical run program for plasmid DNAs in *E. coli* ranging from 2–10 kb might be:

1. Lysis of 500 microliters of bacterial samples and incubation for 5 minutes with proteinase K.
2. Loading and separation at 120 volts for 25 minutes.
3. Activation of microchamber block solenoid.
4. Elution at 120 volts for 20 minutes, followed by draining.
5. Sample removal. (Total time 50 minutes).

EXAMPLE

1. *E coli* strain DH10B (Gibco/Bethesda Research Laboratories) containing the 3.0 kilobase pair plasmid Bluescript (Stratagene, San Diego, Calif.) was inoculated into 50 ml of Circle Grown medium (Bio-101, San Marcos, Calif.) containing 50 microgram/ml of ampicillin and grown in a gyratory shaker for 14 hours at 37 degrees C.

2. A cassette with identical lanes with dimension 0.28" width×0.35" height×1.3" length was prepared containing 1% agarose (Amresco Type 1, Solon, Ohio) in 0.02 M Tris-acetate, 0.0005 M EDTA and with a microchamber in place with attached membrane (BioDesign of New York, Carmel, N.Y.). The dialysis membrane had been soaked for 16 hours in sterile water and rinsed prior to use.

3. To several 0.5 ml aliquots of the above bacterial culture 0.05 ml of 10% triton X-100, 25 mM Tris-HCl pH 8.0, 50 mM EDTA and 200 micrograms/ml of RNase A (Amresco) was added. The sample was thoroughly mixed on a vortexer and allowed to stand for 2 minutes.

4. To the above 8 microliters of 10 mg/ml of proteinase K (Amresco) was added and the solution mixed and incubated at room temperature for 5 minutes.

5. Identical samples of the above treated lysate were loaded in separate wells of the gel cassette and running buffer (20 mM Tris-acetate, 0.0005 M EDTA pH 8.3) added to the electrophoresis rig to a level just cover the cassette with buffer.

6. 120 volts DC was applied for 25 minutes. The microchamber was slid downward in place and 120 volts DC continued or 30 minutes to elute the separated DNA.

7. The running buffer was drained from the electrophoresis chamber 15, the voltage disconnected, and the samples removed simultaneously using a 12 tip multichannel pipettor and pipetted into microtiter wells. Note: the spacing of the lanes, sample chambers, elution chambers and sample removal holes was 0.35 inches from center to center, therefore, the a standard multichannel pipettor was capable of removing all samples at one time.

8. One half of the approx. 60 microliters of purified DNA was mixed with loading buffer containing glycerol and dye and run on a 1% neutral agarose gel containing ethidium bromide. The resulting gel was compared to a set of DNA molecular weight standards (the one kilobase ladder from Bethesda Research Labs). The results demonstrated that the plasmid DNA is nearly 100% supercoiled form and is virtually devoid of chromosomal DNA and RNA. The yield from 0.5 ml of bacterial culture is estimated to be approximately 6 micrograms, therefore, 12 micrograms/ml of culture. Growth of culture in 15 ml culture tubes gives similar yield as grown in erlenmeyer flasks provided that adequate agitation and airation of the culture occurs. I have also found that growth in less rich broth give much poorer yields.

9. One-fourth of the purified DNA from above was cut with the restriction endonuclease BamHl, Eco Rl, Pvu II, Sal I, and Hind III and run on a 1% neutral agarose gel in 1× TAE buffer containing ethidium bromide (see FIG. 3b). The data in this figure demonstrates that the DNA can be cut in the form taken directly from the sample chamber with restriction enzymes typically used in molecular cloning work.

10. 1 microgram of the remaining DNA purified by the above instrumented procedure was subjected to DNA sequencing using the Sequenase (trademark) version 2.0 kit form United States Biochemical (Cleveland, Ohio) 35-S deoxyadenosine triphosphate was used as the radioactive label in the sequencing reactions which were resolved on a 6% polyacrylamide urea gel (0.4 mm thickness) at 35 watt constant power. The gel was fixed according to the Sequenase (trademark) kit manual protocol, dried and autoradiographed with Hyper Paper (trademark) Sequencing film (Amersham, Arlington Heights, Ill.). The result is a highly resolved sequence gel from which I gave 210 nucleotides of readable sequence from one loading of the sequencing reactions.

11. Another portion of plasmid DNA from the above reaction (approximately 1 microgram) was submitted for sequencing on an Applied Biosystems (Foster City, Calif.) model 373A automated DNA sequencer. The resulting instrumented output allowed a read length of over 530 nucleotides with approximately 10 uncertain calls in the sequence. Data not shown. This result demonstrates that the DNA is pure enough to be sequenced by the automated sequencer instrument.

In addition to the above, I transformed one nanogram of purified plasmid DNA in high efficiency competent *E. coli*. purchased from Bethesda Research Laboratories. A control plasmid DNA (pBR322) was transformed along side. I used the transformation protocol provided with the competent cells. The instrument purified Bluescript plasmid gave $8.2 \times 10^5$ colonies per nanogram ($8.2 \times 10^8$ colonies/microgram) of DNA while the pBR322 DNA gave $1.2 \times 10^6$ colonies per nanogram ($1.2 \times 10^9$). Therefore, the plasmid DNA purified by the above procedure can be used for high efficiency *E. coli* transformation.

An optical density spectrum was read on the above DNA which shows an $O.D._{260}/O.S._{280}$ ratio of 2.1. The spectral result indicates that the DNA is as pure as that isolated by conventional methods.

Purification of Cosmid from *E. coli* Cultures

Purification of 30–45 kilobase pair cosmids from *E. coli* cultures using the present invention instrument is accomplished in the same manner as described above, using the sample lysis buffer, except that the separation time is lengthened to 50 minutes (or a voltage program which will cause the 30–45 kb DNA to migrate nearly through the separation gel) and the elution time to 30–45 minutes. Preparation of cosmid DNA using the above described prototype instrument has been accomplished, and the resulting DNA of comparable purity to the plasmid DNA described.

Purification of Genomid DNA from Prokaryotic or Eukaryotic Cells

Purification of high molecular weight DNA from bacterial or mammalian cells using the present invention instrument is accomplished in the same manner as described above, except that the separation time is lengthened to cause the DNA to migrate nearly through the separation gel, typically 70 minutes, and the elution time to 30–45 minutes. Preparation of genomic DNA using the above described prototype instrument has been accomplished and the resulting DNA of comparable purity to the plasmid DNA described. The procedure for preparation of genomic DNA differs from the above procedure in that the lysis protocol must be varied to suit the cell type that is being lysed. For mammalian cells grown in cell culture, the above lysis buffer(s) will be suitable. For other cells, tissue, yeast, and most bacteria (other than *E. coli*) alternate procedures commonly used to break these cell wall types must be used.

The invention herein is also applicable for purification of other kinds of DNA, including but not limited to M13 phage DNA or lambda phage DNA.

While I have illustrated and described my invention by means of specific embodiments, it should be understood that numerous changes and modifications may be made therein without departing from the spirit and scope of the invention as defined in the appended claims. The above specification together with the accompanying drawings contains a written description of the invention and the manner and process of making and using it, in such full, clear, concise, and exact terms as to enable any person skilled in the art to which it pertains, or with which it is most nearly concerned, to make and use the same, and further it sets forth the best mode contemplated by me for carrying out the invention.

I claim:

1. A purification apparatus for the purification of DNA and the like comprising:
   a housing forming a chamber having a front end and a back end for containing a buffer solution;
   means for circulating a buffer within said chamber;
   disposable cassette means positionable within said housing chamber having a front end and a back end having first means including a gel for defining a first path extending between said front end and said back end, inlet means at said front end for introducing a bacterial sample into said path at said front end thereof, an outlet means communicating with said gel at said back end, and second means for defining a second path for extending from said outlet means of said first path via an elution chamber at said back end to a collection chamber, said disposable cassette means comprises a first body formed of a non-conductive material with spaced apart upper and lower panels for containing said gel for defining said first path, said inlet means for introducing a sample at said front end comprises an opening in said upper panel, said second means comprises a second body having a passage defining said elution chamber and having an inlet for communicating with said outlet, and selectively moveable into and out of a position in communication with said outlet means; and
   means for selectively applying an electrical potential along each of said paths for selectively moving a plasmid first along said first path from said bacterial sample to the intersection of said first path then along said second path to said collection window at the end thereof.

2. A purification apparatus according to claim 1 wherein said inlet means includes means extending upward from around said opening for defining said inlet means, upstanding walls surrounding said outlet for defining a well for receiving said second body.

3. A purification apparatus according to claim 2 wherein said first body is formed of a plurality of said first paths and said second body is formed with a plurality of said second paths.

4. A purification apparatus according to claim 3 wherein said first body has a generally rectangular box-like configuration and said gel is an electrophoretic agarose gel.

5. A purification apparatus for the purification of DNA and the like comprising:
   a housing forming a chamber having a front end and a back end for containing a buffer solution;
   means for circulating a buffer within said chamber;
   disposable cassette means positionable within said housing chamber having a front end and a back end and having first means including a gel for defining a first path extending between said front end and said back end, inlet means at said front end for introducing a bacterial sample into said path at said front end thereof, an outlet means communicating with said gel at said back end, and second means for defining a second path for extending from said outlet means of said first path via an elution chamber at said back end to a collection chamber, said first means is a body having a generally rectangular box-like configuration and is formed of a plurality of said first paths and said second means is a body having a plurality of said second paths; and
   means for selectively applying an electrical potential along each of said paths for selectively moving a plasmid first along said first path from said bacterial sample to the intersection of said first path then along said second path to said collection window at the end thereof.

6. A purification apparatus according to claim 5 wherein said means for selectively applying an electrical potential along each of said paths comprises a source of variable electrical power, and means for selectively varying said electrical power.

7. A purification apparatus for the purification of DNA and the like comprising:
   a housing forming a chamber having a front end and a back end for containing a buffer solution;
   means for circulating a buffer within said chamber;
   disposable cassette means positionable within said housing chamber having a front end and a back end having first means including a gel for defining a first path extending between said front end and said back end, inlet means at said front end for introducing a bacterial sample into said path at said front end thereof, an outlet means communicating with said gel at said back end, and second means for defining a second path for extending from said outlet means of said first path via an elution chamber at said back end to a collection chamber, said disposable cassette means comprises a first body formed of a non-conductive material with spaced apart upper and lower panels, a plurality of separating walls between said upper and lower panels defining channels for containing said gel and defining a plurality of said first paths, said inlet means for introducing a sample at said front end comprises an opening in said upper panel into each of said channels, said second means comprises a second body having a plurality of passages defining a plurality of said elution chambers, each having an inlet for communicating with an outlet of said channels, and said second body selectively moveable into a position in communication with said outlet means; and
   means for selectively applying an electrical potential along each of said paths for selectively moving a plasmid first along said first path from said bacterial sample to the intersection of said first path then along said second path to said collection window at the end thereof.

8. A purification apparatus according to claim 7 wherein said means for selectively applying an electrical potential along each of said paths comprises a source of variable electrical power, and means for selectively varying said electrical power.

9. A purification apparatus according to claim 8 wherein said control means includes a programmable CPU and means for programming said CPU for periodic adjustment of said electrical potential.

10. An apparatus for the purification of DNA and the like comprising:
  a generally box-like housing having a chamber for containing a buffer solution;
  means for circulating a buffer to said chamber;
  a disposable cassette detachably mountable within said chamber and having a pair of vertically spaced horizontally extending walls, an electrophoretic gel disposed between said walls for defining at least a part of a first path extending generally horizontally between an inlet at a front end and an outlet at a back end of said chamber, an inlet well for introducing a bacterial sample into said path at said inlet end thereof, and an elution well at said outlet;
  an elution chamber assembly comprising a body having a passage defining an elution chamber and a collection chamber positionable in said elution well in communication with said outlet for defining a second path intersecting said first path and extending to said collection chamber; and
  means for selectively applying an electrical potential along each of said paths for selectively moving a plasmid first along said first path from said inlet well to said elution chamber, then along said second path to said collection chamber at the end thereof.

11. A purification apparatus according to claim 10 wherein said disposable cassette includes a plurality of vertically extending walls disposed between said vertically spaced horizontally extending walls forming a plurality of said first paths, said body includes passage means forming a plurality of said second paths and a collection window comprising a dialysis membrane covering an outlet opening to said passage means.

12. A purification apparatus according to claim 11 wherein said plurality of vertically extending walls extend beyond said outlet into said elution well; and
  said body includes a plurality of slots in a wall thereof for receiving the walls extending into said elution well.

13. A purification apparatus according to claim 12 wherein said means for selectively applying an electrical potential along each of said paths comprises a source of variable electrical power, and means for selectively varying said electrical power.

14. A purification apparatus according to claim 11 wherein said control means includes a programmable CPU and means for programming said CPU for periodic adjustment of said electrical potential.

15. A process for the purification of DNA and the like comprising the steps of:
  providing a housing having walls forming a chamber having a front and a back for containing a buffer solution;
  providing disposable cassette means having an inlet end with inlet means and an outlet end with outlet means and a gel defining a first path extending from said inlet to said outlet, and elution chamber means having an elution chamber and a collection chamber moveable to a position for defining a second path intersecting said first path at said outlet;
  introducing a bacterial sample into said path at said inlet means;
  circulating a buffer into said chamber in contact with said gel; and
  selectively applying an electrical potential along each of said paths for selectively moving a plasmid along said first path from said bacterial sample to said outlet, moving said elution means into position intersecting said first path, applying an electrical potential along said second path for moving said plasmid along said second path to said collection window at the end thereof.

16. A purification process according to claim 15 wherein:
  said disposable cassette means comprises a first body formed of a non-conductive material with spaced apart upper and lower panels, a plurality of separating walls between said upper and lower panels defining channels for containing said gel and defining a plurality of said first paths, said inlet means for introducing a sample at said front end comprises an opening in said upper panel into each of said channels; and
  said elution chamber means comprises a second body having a plurality of passages defining a plurality of said elution chambers, each having an inlet for communicating with an outlet of said channels.

17. A purification process according to claim 16 wherein said applying an electrical potential along each of said paths is carried out by providing a source of variable electrical power, and control means for selectively varying said electrical power.

18. A purification process according to claim 17 wherein said control means includes a programmable CPU and means for programming said CPU for periodic adjustment of said electrical potential.

19. A purification apparatus according to claim 1 wherein said means for selectively applying an electrical potential along each of said paths comprises a source of variable electrical power, and means for selectively varying said electrical power.

20. A purification apparatus according to claim 19 wherein said control means includes a programmable CPU and means for programming said CPU for periodic adjustment of said electrical potential.

21. A purification apparatus according to claim 5 wherein said inlet means includes means extending upward from around said opening for defining said inlet means, upstanding walls surrounding said outlet for defining a well for receiving said second body.

22. A purification apparatus according to claim 6 wherein said control means includes a programmable CPU and means for programming said CPU for periodic adjustment of said electrical potential.

* * * * *